United States Patent [19]

Cerny

[11] Patent Number: 5,376,064

[45] Date of Patent: Dec. 27, 1994

[54] INFLATABLE PROSTHESIS

[75] Inventor: David E. Cerny, Lilburn, Ga.

[73] Assignee: Bard International, Inc., Murray Hill, N.J.

[21] Appl. No.: 157,958

[22] Filed: Nov. 24, 1993

[51] Int. Cl.⁵ .............................. A61F 2/02
[52] U.S. Cl. ...................... 600/30; 600/38; 128/DIG. 25
[58] Field of Search ................ 600/29–31, 600/38–41; 128/DIG. 25; 606/191–199; 604/104, 280–281

[56] References Cited

U.S. PATENT DOCUMENTS

4,934,999  6/1990  Bader ............................ 600/29

Primary Examiner—William E. Kamm
Assistant Examiner—J. P. Lacyk
Attorney, Agent, or Firm—Jones & Askew

[57] ABSTRACT

An inflatable prosthesis is disclosed which comprises a structural member having a bore dimensioned to receive a needle formed in its back end. An elastomeric balloon has a back end in sealing engagement with the structural member and has a front end extending beyond the front end of the structural member such that a portion of the structural member is contained within the balloon. A port is defined in the structural member for placing the bore in fluid communication with a port location exterior of the structural member which is contained within the balloon, whereby fluid infused into the bore passes through the port and into a space between the balloon and the exterior surface of the structural member to inflate the balloon. An elastomeric member has one portion attached to the structural member and another portion attached to the front end of the balloon so as to partially constrain axial expansion of the prosthesis as the balloon is inflated.

7 Claims, 10 Drawing Sheets

Fig. 12

INFLATABLE PROSTHESIS

TECHNICAL FIELD

The present invention relates generally to medical devices and procedures. More specifically the present invention relates to an inflatable prosthesis for implantation within the periurethral tissues of a patient to treat urinary incontinence.

BACKGROUND OF THE INVENTION

It is known to implant inflatable prostheses in the periurethral tissues of a patient to provide support to the urethral sphincter as a treatment for urinary incontinence. Such implants are described, for example, in U.S. Pat. No. 4,832,680 to Haber et al. The prostheses, similar to tiny balloons, are introduced into the periurethral tissues and positioned, one on either side of the urethra, in an uninflated condition. The prostheses are then inflated by infusing saline solution through a cannula. As the prostheses expand they exert pressure and cause coaptation of the urethra.

The inflatable prostheses normally used for this procedure comprise a balloon mounted around a main body and anchored to the body at its rearward end. As the balloon is inflated, the major direction of elongation is longitudinal, that is, parallel to the urethra. Thus if the prostheses are not positioned closely enough to the urethra, or if the periurethral tissues tend to be inelastic, as in the case of scar tissue from previous surgery or radiation treatment, considerable additional inflation of the prostheses is required to result in relatively minor increases in coaptative pressure.

Inflatable prostheses are known which expand primarily in a radial direction. Such prostheses are disclosed, for example, in U.S. Pat. No. 3,834,394 to Hunter et al. These prostheses comprise a balloon whose opposite ends are linked to prevent axial elongation. As the balloon is first inflated, the only possible direction of expansion is radially. The inflatable prosthesis of the aforementioned U.S. Pat. No. 3,834,394 is disclosed only with respect to vascular applications. Furthermore, even though such a prosthesis might provide advantages in terms of enhanced lateral pressure, the pressure tends to be exerted at only a single point.

Thus there is a need for an improved inflatable prosthesis which when positioned within the periurethral tissues will exert radial pressure against the urethra but which will exert that pressure along a substantial length of the urethra.

Them is a further need for an inflatable prosthesis for implanting in periurethral tissues which will expand in such a way as to provide a greater margin of error with respect to placement of the devices.

Them is also a need for an inflatable implant which expands primarily radially but which exhibits some limited degree of longitudinal expansion.

SUMMARY OF THE INVENTION

As will be seen, the present invention overcomes these and other problems associated with prior art inflatable implants. Stated generally, the inflatable implant of the present invention is adapted to treat urinary incontinence when positioned within the periurethral tissues inflates in such a manner as to exert a radial pressure against the urethra and exerts that pressure along a substantial length of the urethra. The implant expands in such a way as to provide a greater margin for error in placement of the device by expanding primarily radially while exhibiting a limited degree of axial elongation.

Stated more specifically, the present invention comprises an inflatable prosthesis comprising a structural member having a bore formed in its back end dimensioned to receive a needle. An elastomeric balloon has a back end in sealing engagement with the structural member and has a front end extending beyond the front end of the structural member such that a portion of the structural member is contained within the balloon. A port is defined in the structural member for placing the bore in fluid communication with a port location exterior of the structural member which is contained within the balloon, whereby fluid infused into the bore passes through the port and into a space between the balloon and the exterior surface of the structural member to inflate the balloon. An elastomeric member has one portion attached to the structural member and another portion attached to the front end of the balloon so as to partially constrain axial expansion of the prosthesis as the balloon is inflated.

In a preferred embodiment the elastomeric member comprises an elastomeric tubular housing sealed to the perimeter of the structural member at a location rearward of the port location. The elastomeric tubular housing is stretched against the exterior surface of the structural member and has a hole formed therethrough at a location removed from the port location. When fluid exits the port under pressure, it distends the housing and passes between the exterior surface of the structural member and the housing to pass through the hole into the balloon. The elastomeric housing returns against the exterior surface of the structural member upon release of the pressure to prevent fluid from returning back through the port, whereby the balloon is maintained in an inflated state.

In another aspect of the preferred embodiment, the structural member comprises a needle guide having a longitudinal bore formed therewithin and having at least one radial port formed in a side wall thereof. A needle guide core has a portion disposed within the central longitudinal bore of the needle guide and is pierceable by a needle. The needle guide core has a transverse bore in communication with the radial port of the needle guide such that fluid infused by a needle inserted in the longitudinal bore of the needle guide passes through the transverse bore of the needle guide core and through the radial port of the needle guide.

Thus it is an object of the present invention to provide an improved inflatable prosthesis which when positioned within the periurethral tissues will exert radial pressure against the urethra but which will exert that pressure along a substantial length of the urethra.

It is a further object of the present invention to provide an inflatable prosthesis for implanting in periurethral tissues which will expand in such a way as to provide a greater margin of error with respect to placement of the devices.

It is also an object of the present invention to provide an inflatable implant which expands primarily radially but which exhibits some limited extent of axial elongation.

Other objects, features, and advantages of the present invention will become apparent upon reading the following specification, when taken in conjunction with the drawings and the appended claims.

DETAILED DESCRIPTION OF THE DISCLOSED EMBODIMENT

Figure 1:
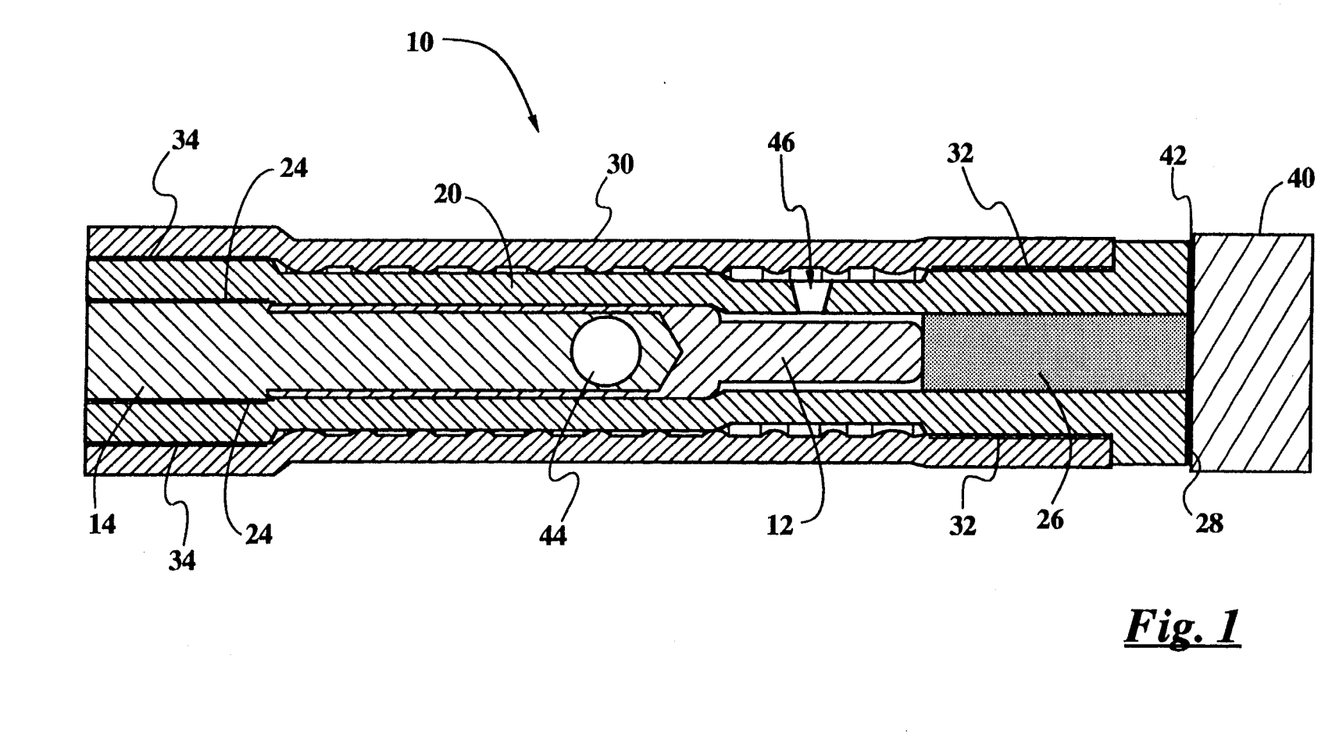
FIG. 1 is a cross-sectional view of an inflatable prosthesis according to the present invention.

Referring now in more detail to the drawings, in which like numerals indicate like elements throughout the several views, FIG. 1 shows an inflatable prosthesis 10 according to the present invention. A needle guide 12 has a needle guide core 14 mounted thereto.

An inner housing 20 in the shape of a generally tubular sleeve fits over the needle guide 12 and needle guide core 14. The inner housing 20 is bonded to the needle guide core 14 at a bonding location 24 adjacent the rearward ends the needle guide 12 and inner housing 20. A plug 26 disposed within the inner housing 20 adjacent the forward end 28 of the inner housing.

A balloon 30 in the shape of a generally tubular sleeve is disposed around the inner housing 20 and is bonded to the inner housing at a forward bonding location 32 and at rearward bonding location 34. The balloon 30 is bonded aroused the entire periphery of the inner housing 20 at the two bonding locations 32, 34 so as to form an airtight seal between the balloon and the inner housing between the two bond locations 32, 34.

A cylindrical felt plug 40 comprised of a suitable material such as polyethyleneterephthalate is bonded to the forward end of the plug 26 and to the forward end 28 of the inner housing 20 at a bonding location 42. The purpose of the felt plug 40 is to promote tissue ingrowth and to inhibit migration of the inflatable prosthesis 10 once implanted.

A radial port 44 is formed through the needle guide 12 and needle guide core 14. An orifice 46 is formed in the wall of the inner housing 20 at a location which is both axially and angularly offset from the port 44. By means of the ports 44 and orifice 46 the interior of the needle guide 12 is in fluid communication with a location interior of the balloon 30 and exterior of the inner housing 20.

Figure 2A:
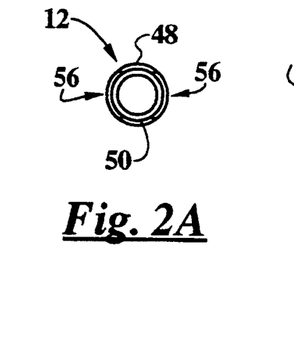
FIG. 2A is an end view of a needle guide of the inflatable prosthesis of FIG. 1.
Figure 2B:
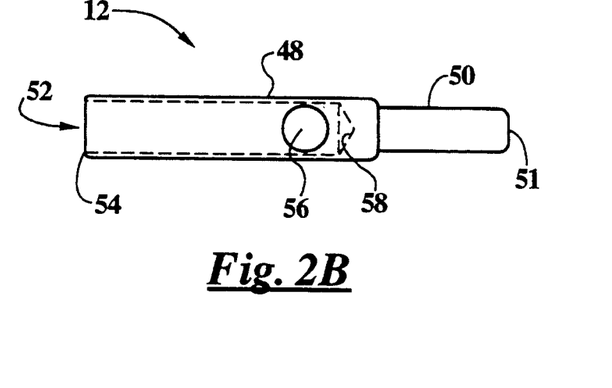
FIG. 2B is a sideview of the needle guide of FIG. 2A.

Referring now to FIGS. 2A and 2B, the needle guide 12 of the disclosed embodiment is comprised of titanium and has a cylindrical main portion 48, a reduced cylindrical forward portion 50, and a forward end 51. The needle guide 12 has an axial bore 52 formed in its rearward end 54. Opposed radial holes 56 are formed through the walls of the needle guide 12 and intersect the bore 52 adjacent its forward end 58.

Figure 3A:
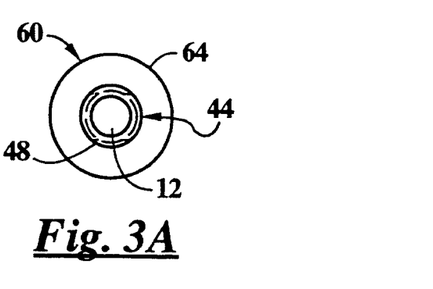
FIG. 3A is an end view of the needle guide of FIGS. 2A-B with a needle guide core molding installed therein.
Figure 3B:
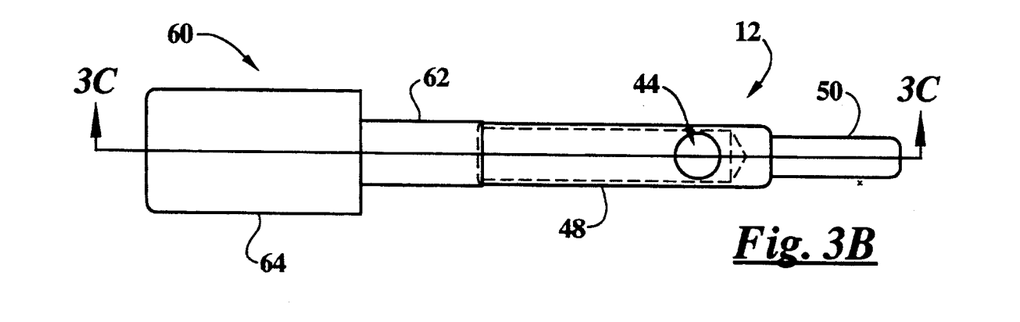
FIG. 3B is a sideview of the needle guide and needle guide core molding of FIG. 3A.
Figure 3C:
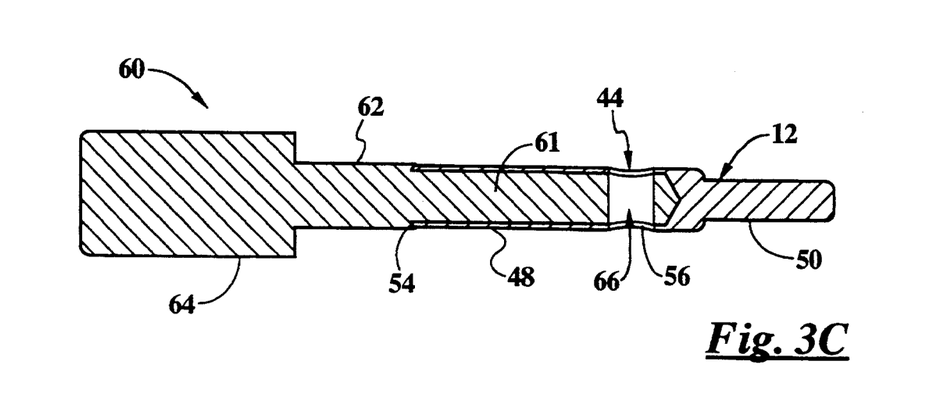
FIG. 3C is a cross-sectional view taken along line 3C—3C of FIG. 3B.

FIGS. 3A-C depict a needle guide core molding 60 assembled to the needle guide 12. The needle guide core molding 60 is formed from Dow Corning Q7-4720 silicone. The needle guide core molding 60 has a forward portion 61 disposed within the longitudinal passage 52 (FIGS. 2A-B) of the needle guide 12. An intermediate portion 62 of the needle guide core molding 60 is disposed immediately rearward of the rear end 54 of the needle guide 12 and has an outer diameter corresponding to that of the cylindrical main portion 48 of the needle guide 12. An enlarged rear portion 64 of the needle guide core molding 60 will eventually be trimmed away to form the completed needle guide core 14 but provides a convenient means for handling the needle guide 12 and needle guide core molding 60 during assembly.

A transverse bore 66 is formed in the forward portion 61 of the needle guide core molding 60 between the opposed holes 56 in the cylindrical main portion 48 of the needle guide 12. In combination, the holes 56 in the needle guide 12 and the transverse bore 66 in the needle guide core molding 60 form the radial port 44.

Figures 4A, 4B:
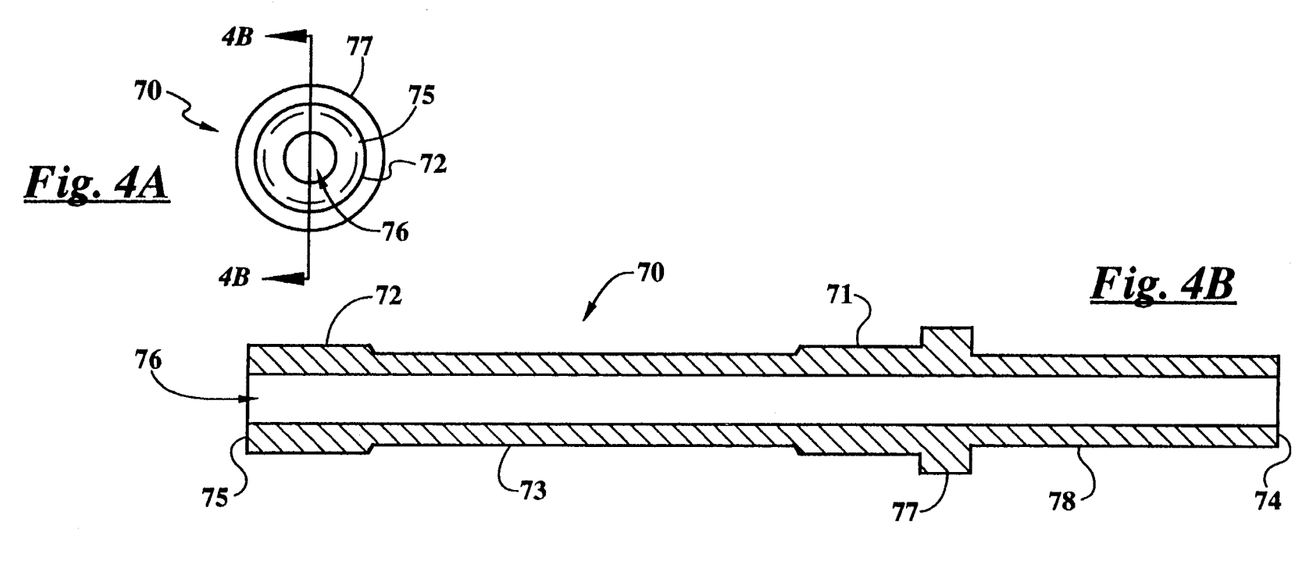
FIG. 4A is an end view of an inner housing molding used to manufacture the inflatable prosthesis of FIG. 1.
FIG. 4B is a cross-sectional view taken along line 4B—4B of FIG. 4A.

Referring now to FIGS. 4A-B, an inner housing molding 70, formed from Dow Corning Q7-4735 silicone, takes the form of a generally tubular sleeve. The inner housing molding 70 includes forward and rear collar sections 71, 72 joined by an intermediate section 73 of reduced outer diameter. The inner housing molding has a forward end 74 and a rearward end 75. A longitudinal passage 76 extends the length of the inner housing molding 70. An annular flange 77 is formed at the front end of the forward collar section 71. An extension 78 extends forward of the annular flange 77. The extension 78 will be trimmed away as one of the last steps of manufacture to form the inner housing 20 but provides a convenient means for holding the inner housing molding 70 during the manufacturing process.

Figure 5A:
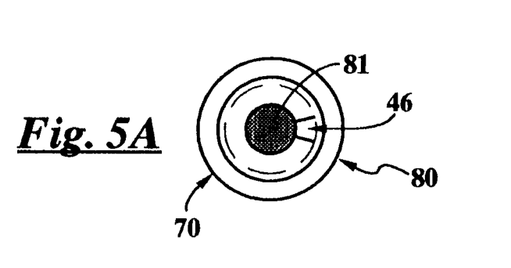
FIG. 5A is an end view of the inner housing molding of FIGS. 4A-B showing a plug disposed within the bore of the inner housing molding and a port formed in the housing molding wall.
Figure 5B:
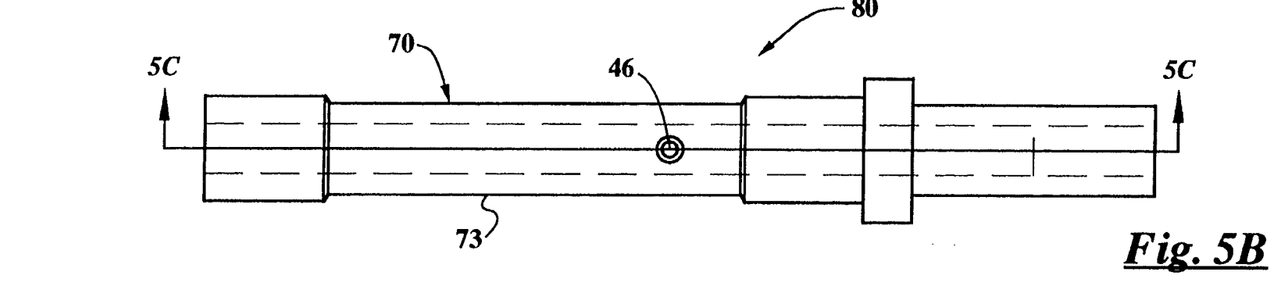
FIG. 5B is a sideview of the inner housing molding and plug of FIG. 5A.
Figure 5C:
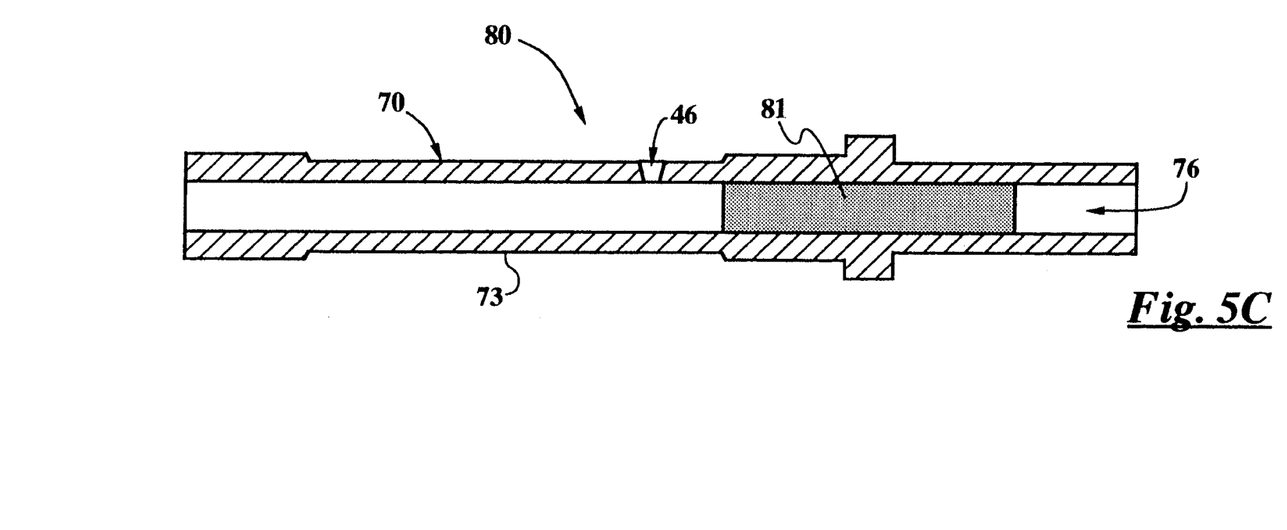
FIG. 5C is a cross-sectional view taken along line 5C—5C of FIG. 5B.

FIGS. 5A-C show an inner housing assembly 80 comprising the inner housing molding 70 with silicone plug insert 81 disposed within the longitudinal passage 76 of the inner housing molding. The plug insert 81 is formed from Dow Corning Q7-4840 silicone. The radially extending orifice 46 is also shown extending through the wall of the reduced intermediate section 73 of the inner housing molding 70.

Figure 6A:
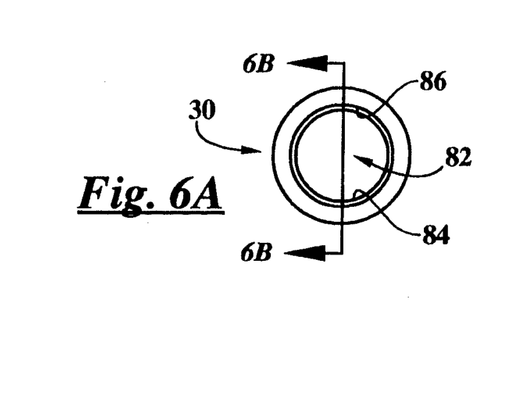
FIG. 6A is an end view of a balloon of the inflatable prosthesis of FIG. 1.
Figure 6B:
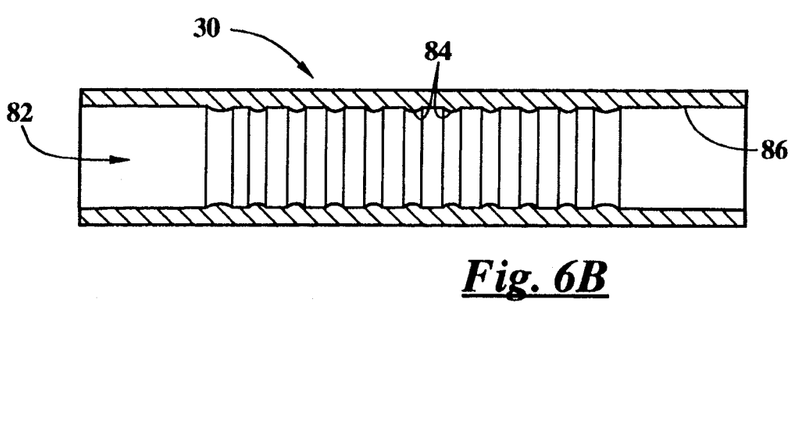
FIG. 6B is a cross-sectional view taken along line 6B—6B of FIG. 6A.

Referring now to FIGS. 6A–B, the balloon 30 is formed from Dow Corning Q7-4720 silicone as a generally tubular sleeve. The balloon has a longitudinally extending passage 82. A plurality of annular ribs 84 are formed on the inner wall 86 of the balloon 30 at longitudinally spaced-apart intervals to promote symmetrical inflation, as will be hereinbelow described.

Manufacture of the inflatable prosthesis 10 will now be explained. Starting with the needle guide of FIGS. 2A–B, a pin (not shown) having an outer diameter corresponding to the inner diameter of the holes 56 in the needle guide main body portion 48 is positioned through one hole 56, through the main body portion 48 of the needle guide 12, and out the opposite hole 56. The needle guide 12 and pin are then placed into a mold which extends beyond the end 54 of the needle guide and has cylindrical cavities of suitable configuration to form the intermediate and rearward portions 62, 64 of the needle guide core 14. Dow Corning Q7-4720 silicone is then injected into the mold, filling the bore 52 of the needle guide 12 except for the space occupied by the pin, and thereby forming the needle guide core molding 60. When the silicone has cured, the pin is removed, leaving the transverse recess 66.

The construction of the inner housing assembly 80 will next be explained. A pin (not shown) having an outer diameter corresponding to the inner diameter of the longitudinal passage 76 in the inner housing molding 70 is inserted into the rearward end 74 of the inner housing molding. A shoulder formed on the pin confronts the rearward end 75 of the inner housing molding 70 and permits only a predetermined length of the pin to be inserted into the inner housing molding. Viscous silicone, preferably Dow Corning Q7-4840 silicone, is then injected into the longitudinal passage 76 of the inner housing molding 70 from the forward end 74 the molding. A second pin having a diameter corresponding to the longitudinal passage 76 of the inner housing molding 70 and having a shoulder formed thereon to engage the forward end 74 of the inner housing molding and thereby limit the length of the pin which can be inserted into the longitudinal passage, is inserted into the forward end 74 of the inner housing molding 70. The entire assemblage, including pins, is then placed into a fixture of predetermined length which exerts an axial compressive force on the pins and imparts pressure on the silicone plug insert 81 during curing. After the silicone plug insert 81 is cured, the pins are removed.

Figure 7:
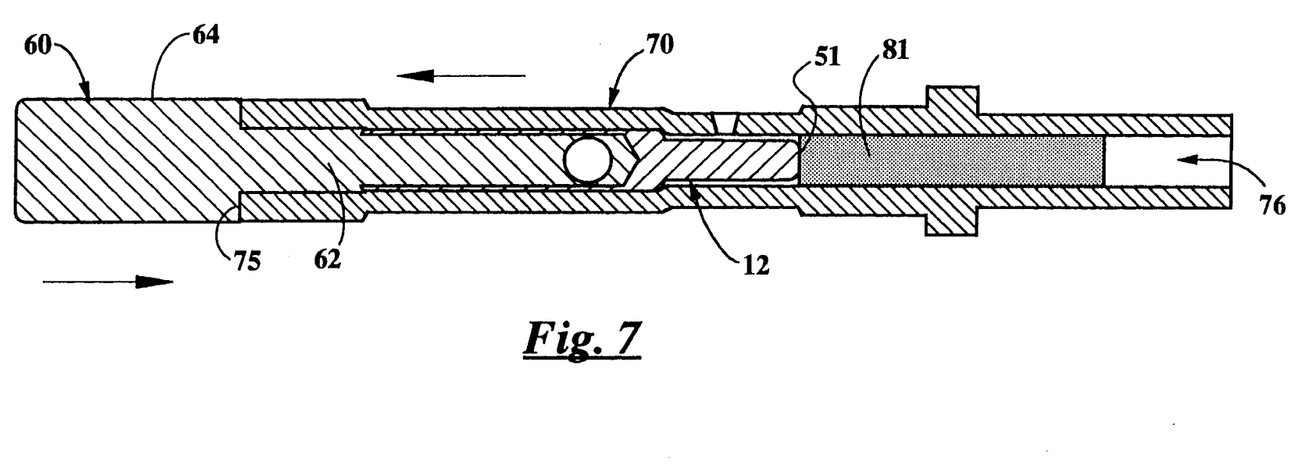
FIG. 7 is a side cutaway view showing the inner housing molding and plug of FIGS. 5A-C being bonded to the needle guide with needle guide core molding of FIGS. 3A-C.

Referring now to FIG. 7, the inner housing molding 70 is now installed onto the needle guide 12 and associated needle guide core molding 60. The inner housing molding 70 is first swelled with a suitable expanding agent, e.g., freon. The rearward end 75 of the inner housing molding 70 with plug insert 81 is then inserted over the forward end 51 of the needle guide 12 and advanced rearward over the intermediate portion 62 of the needle guide core molding 60 until the rearward end of the inner housing molding 70 confronts the enlarged rear portion 64 of the needle guide core molding 60. As the expanding agent evaporates, the inner housing molding returns to its original size fitting tightly against the periphery of the needle guide with needle guide core molding. When the expanding agent has completely evaporated from the inner housing molding 70, a suitable bonding agent, such as Dow Corning Q7-4840 silicone, is applied between the intermediate portion 62 of the needle guide core molding 60 and the overlying portion of the inner housing molding 70.

Figure 8:
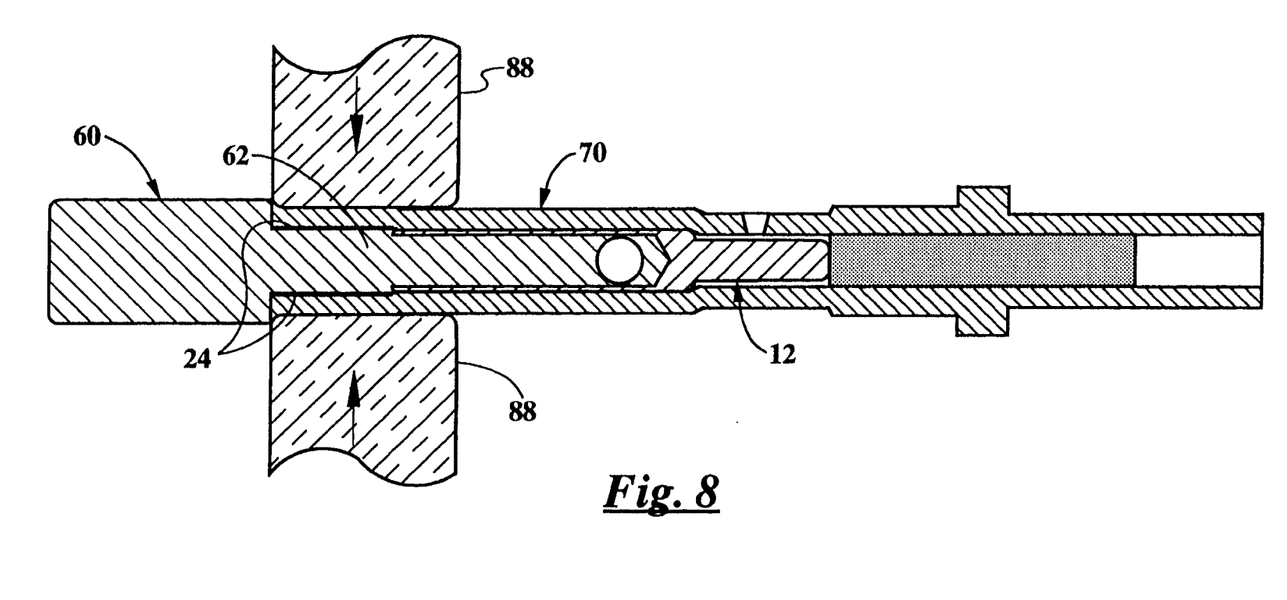
FIG. 8 is a side cutaway view showing the assembly of FIG. 7 with pressure being applied to the bond.

As next shown in FIG. 8, heat and radially inward pressure are applied around the periphery of the inner housing molding 70 adjacent the bond location 24 until the silicone bond has cured. In the disclosed embodiment a gluing fixture 88 heated to a temperature of 260°–270° F. is applied to the periphery of the inner housing molding 70 for approximately four minutes with sufficient force to compress the diameter of the assembly by 0–10% of its uncompressed diameter.

Figure 9:
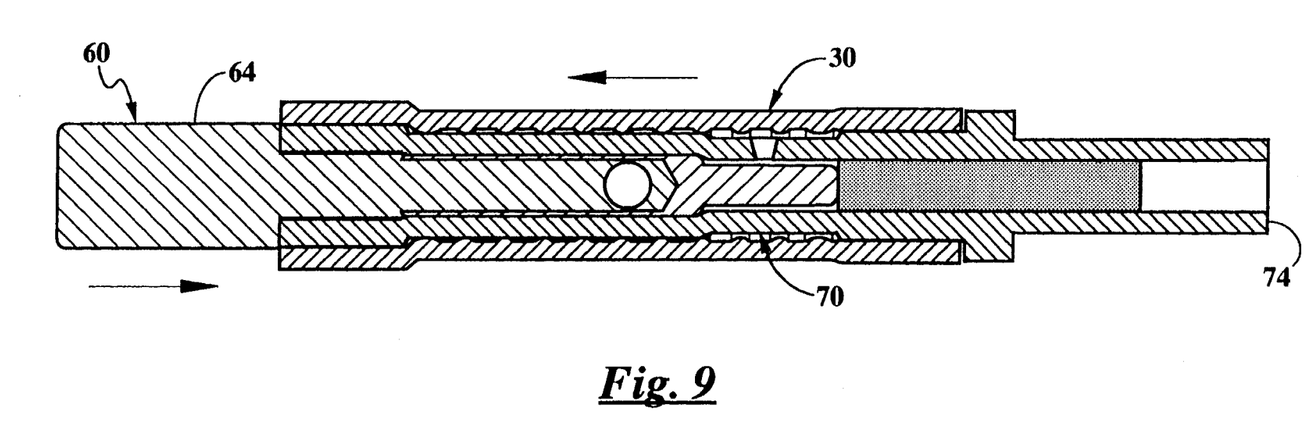
FIG. 9 is a side cutaway view showing the balloon of FIG. 6A-B being bonded to the assembly of FIG. 7.
Figure 10:
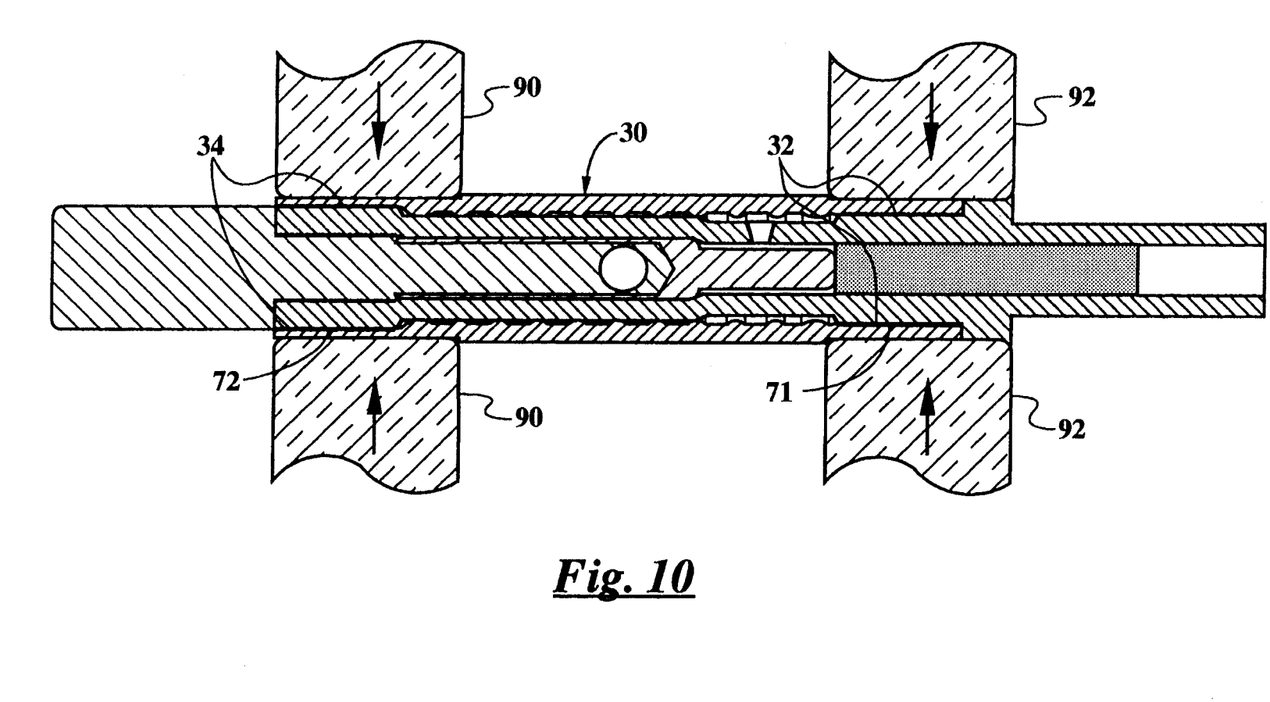
FIG. 10 is a side cutaway view of be assembly of FIG. 9 showing pressure being applied to the bonds.

Referring now to FIG. 9, the balloon 30 is next installed onto the inner housing molding 70. The balloon 30 is first swelled with a suitable expanding agent, e.g., freon. The expanded balloon 30 is then slipped over the forward end 74 of the inner housing molding 70 and advanced longitudinally rearward over the inner housing molding until the leading edge of the balloon bottoms out against the enlarged rear portion 64 of the needle guide core molding 60. After the expanding agent has evaporated from the balloon, a silicone such as Dow Corning Q7-4840 silicone, is applied between the collars 71, 72 of the inner housing molding 70 and the overlying portions of the balloon 30. Then, as shown in FIG. 10, heat and radially inward force are applied to the periphery of the balloon 30 at the front and rear bond locations 32, 34. In the preferred embodiment, the heat and radially inward force are applied by means of a pair of gluing fixtures 90, 92, which are heated to a temperature of 260°–270° F. and applied to the periphery of the balloon 30 for approximately four minutes with sufficient force to compress the diameter of the assembly by up to 10% of its uncompressed diameter.

Figure 11:
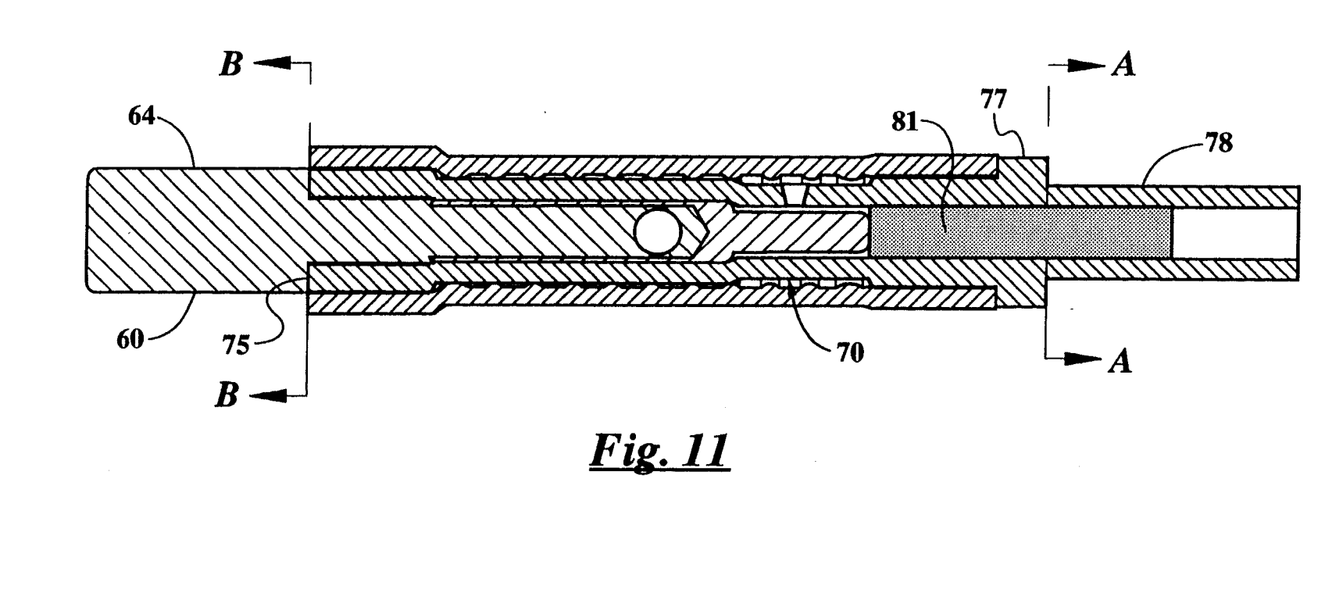
FIG. 11 is a side cutaway view of the assembly of FIG. 9 showing how excess portions of the needle guide core molding and inner housing molding and plug are trimmed away to complete the assembly of the inflatable prosthesis.

The final step in the manufacturing process is illustrated in FIG. 11. The forward portion 78 of the inner housing molding 70 and the portion of the silicone plug insert 81 lying therewithin are trimmed off along a transverse plane indicated by the line A—A, which plane is coincident to the forward edge of the annular flange 77. Similarly, the rear portion 64 of the needle guide core molding 60 is trimmed away along the transverse plane indicated by the line B—B, which plane is coincident to the rearward edge 75 of the inner housing molding 70. The cylindrical felt plug 40 (FIG. 1) is then bonded to the forward end of the structure at the bonding location 42 to complete the assembly of the inflatable prosthesis 10 depicted in FIG. 1.

Figure 12:
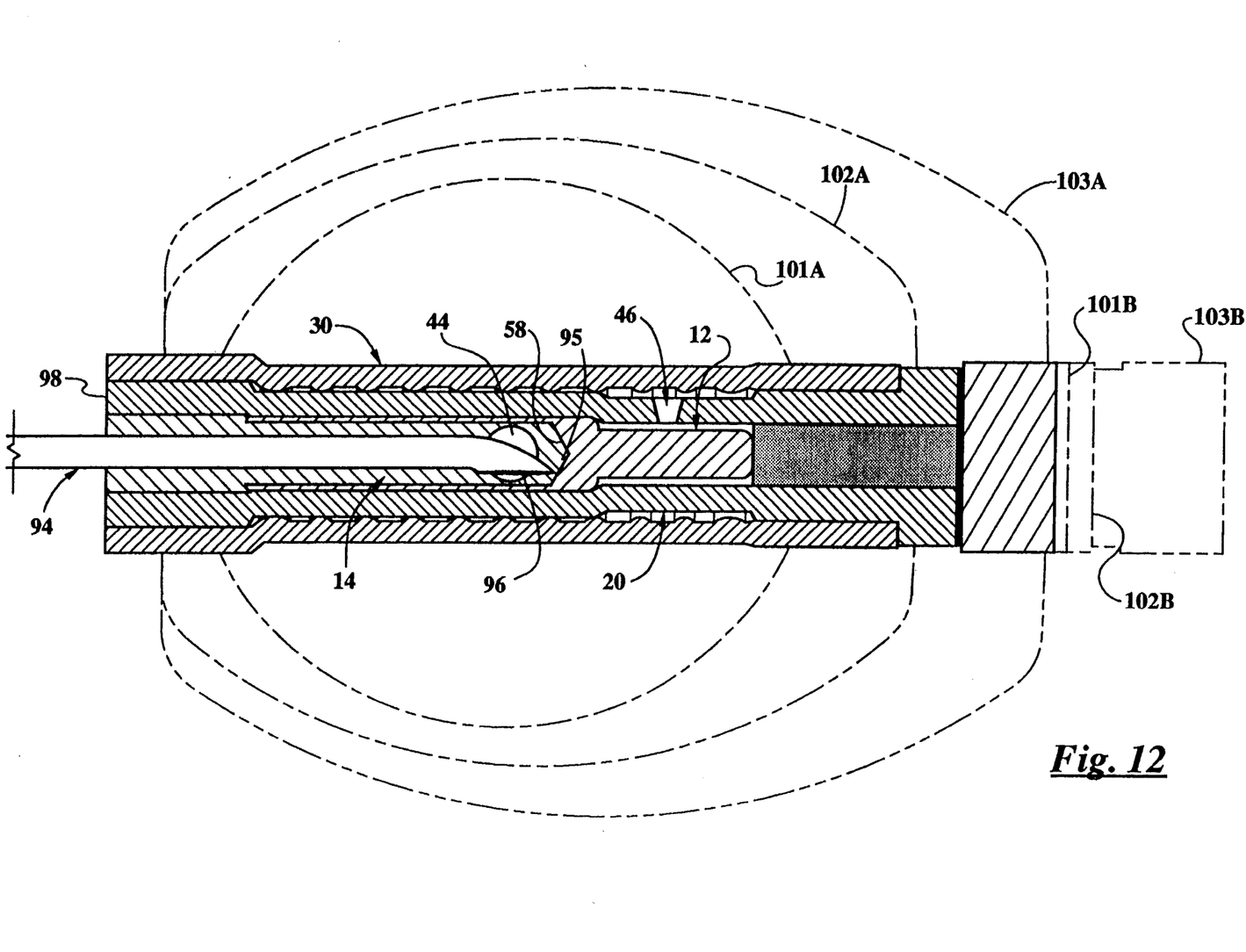
FIG. 12 is a side cutaway view of the inflatable prosthesis of FIG. 1 showing a needle inserted into the needle guide with needle guide core and depicting the prosthesis in varying stages of inflation.

Inflation of the prosthesis 10 is illustrated in FIG. 12. A non-coring needle 94 having a forward end 95 and an orifice 96 adjacent the forward end is inserted into the needle guide core 14 from the rearward end 98 of the prosthesis 10. The needle is in fluid communication with a syringe (not shown). The needle 94 is advanced until its forward end 95 bottoms out against the forward end 58 of the longitudinal bore 52 of the needle guide 12. In this position the orifice 96 at the forward end 95 of the needle 94 is axially aligned with the radial port 44 formed through the needle guide 12 and needle guide core 14.

A suitable inflation medium such as a saline solution is then infused from the syringe through the needle 94. The inflation medium exits the orifice 96 of the needle 94 and passes through the radial port 44 in the needle guide 12 and needle guide core 14. Fluid pressure distends the inner housing 20 slightly outward, and the inflation medium passes between the needle guide 12 and the distended inner housing 20, exits through the orifice 46 in the wall of the inner housing, and passes into the space between the inner housing 20 and the balloon 30. As the inflation medium is infused through the needle and along the fluid path into the balloon 30, the balloon begins to inflate.

As shown in FIG. 12, the elastic character of the inner housing 20 partially constrains axial elongation of the prosthesis 10 as the balloon 30 is inflated but permits some expansion in the axial direction. The dashed line 101A illustrates the configuration of the balloon 30 of the inflatable prosthesis 10 when 1 cc of the inflation medium has been infused, and the dashed line 101B illustrates the position of the forward end 100 of the prosthesis at that stage of inflation. As can be seen, the primary direction of expansion is radially outward, with only a minor elongation of the prosthesis in the axial direction.

The dashed lines 102A, 102B illustrate the configuration of the balloon 30 of the inflatable prosthesis 10 after 2 cc of the inflation medium has been infused, it being understood that the rearward end 98 of the prosthesis 10 remains fixed in location throughout the inflation process as a result of the prosthesis being mounted to the needle 94. At this stage of inflation, the primary direction of expansion is still radially outward, but there is proportionately more elongation of the prosthesis 10 in the axial direction.

The configuration of the prosthesis 10 after infusion of 3 cc of the inflation medium is shown by the dashed lines 103A, 103B. At this stage of inflation, the primary direction of expansion is now in the axial direction, and there is only a minor component of expansion in the radial direction.

When fluid pressure from the syringe is relaxed, the resilient inner housing 20 returns to its normal position imposed tightly around the perimeter of the needle guard 12. This tight fit is further enhanced by the pressure exerted against the outer surface of the inner housing 20 by the inflation medium within the balloon 30. The inner housing 20 thus serves as a checkvalve, preventing the inflation medium within the balloon 30 from returning back through the radial ports 44 and leaking out of the prosthesis 10.

The capability of the prosthesis 10 to expand in both a radial and an axial direction affords certain advantages over prior art inflatable prostheses. Whereas fully constraining axial elongation of a balloon results in all expansion being directed radially outward, and whereas unconstrained axial elongation of a balloon results substantially all of the expansion being directed axially, the partial axial constraint provided by the elastic inner housing 20 causes expansion of the balloon 30 to have significant radial and axial components. When the inflatable prosthesis 10 is, for example, implanted in periurethral tissues to provide support to the urethral sphincter as a treatment for urinary incontinence, expansion of the prosthesis in the axial direction permits the prosthesis to exert a coaptive force along a length of the urethra, rather than at only a single point. However, the fact that the prosthesis 10 still has a component of expansion in the radial direction means that the physician can increase the pressure on the urethra by infusing further inflation medium into the balloon without having to reposition the balloon with respect to the urethra. This capacity to expand in a radial direction provide a greater margin of error with respect to placement of the devices.

The needle valve 12 and needle valve core 14 in combination comprise a main body component of the prosthesis 10. This main body component serves many functions, including providing the foundation for bonding the device assembly, providing a friction fitment for an infusion catheter, providing the inner workings of a check valve mechanism, and serving as a structural member to add rigidity during positioning within the periurethral tissues.

Similarly, the inner housing 20 performs several functions. First, the inner housing serves as a structural member by partially limiting axial elongation of the outer balloon 30 during inflation. The inner housing 20 also operates as an elastic member for the checkvalve mechanism, creating a fluid pathway for the infusion medium.

While the preferred embodiment has been disclosed with respect to components comprised of particular materials, it will be understood that the disclosed materials are illustrative only and are not intended to limit the construction of the invention to any particular materials.

Finally, it will be understood that the preferred embodiment has been disclosed by way of example, and that other modifications may occur to those skilled in the art without departing from the scope and spirit of the appended claims.

What is claimed is:

1. An inflatable prosthesis, comprising:
   a structural member having front and back ends and an exterior surface and having a longitudinal bore formed in said back end of said structural member dimensioned to receive a needle therewithin;
   an elastomeric balloon having a back end in sealing engagement with said structural member and having a front end extending beyond said front end of said structural member such that a portion of said structural member is contained within said balloon;
   said structural member having a port means defined therein for placing said bore in fluid communication with a port location exterior of said structural member which is contained within said balloon, whereby fluid infused into said bore passes through said port means and into a space between said balloon and said exterior surface of said structural member to inflate said balloon; and
   elastomeric means having a rearward portion attached to said structural member at a location rearward of said port means and a forward portion attached to said front end of said balloon for partially constraining axial expansion of said balloon as said balloon is inflated.

2. The prosthesis of claim 1, wherein said structural member comprises a perimeter, and wherein said elastomeric means comprises an elastomeric tubular housing sealed to the perimeter of said structural member at a location rearward of said port location and stretched against said exterior surface of said structural member, said elastomeric tubular housing having a hole formed therethrough at a location removed from said port location such that fluid exiting said port means under pressure distends said housing and passes between said exterior surface of said structural member and said housing to pass through said hole into said balloon, said elastomeric housing returning against said exterior surface of said structural member upon release of said pressure to prevent fluid from returning back through said port means, whereby said balloon is maintained in an inflated state.

3. The prosthesis of claim 2, wherein said elastomeric tubular housing extends forward of said structural member, and wherein said front end of said elastomeric balloon is in sealing engagement with a portion of said elastomeric tubular housing which extends forward of said structural member.

4. The prosthesis of claim 3, wherein a silicone plug is disposed within said tubular housing forward of said structural member.

5. The prosthesis of claim 1, further comprising a felt plug bonded to a front end of said prosthesis.

6. The prosthesis of claim 1,
wherein said structural member comprises a needle guide having a longitudinal bore formed therewithin;
wherein said port means comprises at least one radial port formed in a side wall of said needle guide; and
wherein said structural member further comprises a needle guide core having a portion disposed within said central longitudinal bore of said needle guide, said needle guide core being pierceable by a needle, and said needle guide core having a transverse bore in communication with said at least one radial port of said needle guide.

7. The prosthesis of claim 6, wherein said needle guide core further comprises a portion extending rearward of said needle guide, and wherein said elastomeric means having a rearward portion attached to said structural member at a location rearward of said port means comprises said elastomeric means having a rearward portion attached to said portion of said needle guide core extending rearward of said needle guide.

* * * * *